US00PP08002P

United States Patent [19]

Bradford et al.

[11] Patent Number: Plant 8,002

[45] Date of Patent: Oct. 13, 1992

[54] NECTARINE TREE (SUMMER BLUSH)

[76] Inventors: Lowell G. Bradford, 12439 E. Savana Rd.; Norman G. Bradford, 11875 E. Savana Rd., both of Le Grand, Calif. 95333

[21] Appl. No.: 684,854

[22] Filed: Apr. 15, 1991

[51] Int. Cl.[5] ..... A01H 5/00

[52] U.S. Cl. ..... Plt./41.1

[58] Field of Search ..... Plt./41

[56] References Cited

U.S. PATENT DOCUMENTS

P.P. 3,165 5/1972 Anderson ..... Plt. 41
P.P. 4,792 11/1981 Anderson ..... Plt. 41
P.P. 6,363 11/1988 Bradford et al. ..... Plt. 41

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the second week in August, with first picking on Aug. 10, 1990. The fruit is uniformly large in size, excellent in flavor, attractively globose in shape, clingstone in type, very firm in texture, and full red in skin color. The variety was developed as a hybridized seedling from an unnamed nectarine seed parent and an unnamed nectarine pollen parent. The unnamed pollen parent resulted from a cross of Red Diamond Nectarine (U.S. Plant Pat. No. 3,165) and Aurora Grand Nectarine (U.S. Plant Pat. No. 4,792).

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as ∓Summer Blush". The present variety was hybridized in 1985 by us in a cultivated area of our experimental orchard at Bradford Farms near Le Grand, Calif. in Merced County (San Joaquin Valley). It was the result of an unnamed nectarine seedling as the selected seed parent and another unnamed nectarine seedling as the selected pollen parent. This unnamed pollen parent resulted from a cross of Red Diamond Nectarine (U.S. Plant Pat. No. 3,165) and Aurora Grand Nectarine (U.S. Plant Pat. No. 4,792). Subsequent to origination of the present variety of nectarine tree, we asexually reproduced it by budding and grafting, and such reproduction of plant and fruit characteristics were true to the original plant in all respects.

The fruit produced by the present variety is most similar to that of the August Red Nectarine (U.S. Plant Pat. No. 6,363) by being large in size, very firm in texture, and clingstone in type, but is distinguished therefrom and an improvement thereon by producing fruit that is full red in skin color over the entire fruit surface, that is sweeter in flavor, and that ripens 12 days earlier.

The present variety is similar to both of its pollen grandparents, the Red Diamond (U.S. Plant Pat. No. 3,165) and the Aurora Grand (U.S. Plant Pat. No. 4,792), in fruit appearance by being a full red colored nectarine with excellent firmness, but is very distinguished therefrom by producing fruit that is clingstone instead of freestone and that ripens approximately 42 to 70 days later, respectively.

DRAWING

The accompanying photograph exhibits four whole fruits positioned to display the characteristics of the skin color and form, a sectioned half fruit divided transverse to the suture plane to reveal the flesh, a typical stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Aug. 14, 1990. All major color code designations are by reference to the Inter-Society Color Council, National Bureau of standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Grayish brown [61. gy.Br].
- *Lenticels.*—Numerous. Color: Moderate orange [53. m.o]. Average Size: ¼" [6.4 mm].

Branches:
- *Size.—Medium.*
- *Texture.*—Medium.
- *Color.*—1st year wood topside: Light grayish red [18. l.gy.R]. 1st year wood underside: Brilliant yellow green [116. brill.YG]. Older wood: Moderate brown [58. m.Br].
- *Lenticels.*—Numerous, very small.

Leaves:
- *Size.*—Large. Average length: 6 ¼" [158.8 mm.]. Average width: 1 ⅜" [34.9 mm.].
- Thickness.—Medium.

*Form.*—Elliptical.
*Apex.*—Acuminate.
*Base.*—Acute.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average length: ½" [12.7 mm.]. Average thickness: 1/16" [1.6 mm.]. Dorsal color: Moderate yellow green [120. m.YG]. Ventral color: Grayish yellow green [122. gy.YG].
*Stipules.*—Numerous. Average length: 5/16" [7.9 mm.].
*Glands.*—Average number: 4 per leaf. Position: Mostly oppositely positioned on petiole and base of blade, with a few singles. Size: Medium. Form: Reniform. Color: Light grayish red [18. 1.gy.R].

Flower buds:
*Hardiness.*—Hardy.
*Size.*—Medium.
*Length.*—Medium.
*Form.*—Free.
*Surface.*—Pubescent.

Flowers:
*Blooming period.*—Medium as compared with other varieties.
*Size.*—Small.
*Color.*—Light purplish pink [249. 1.pPK].

FRUIT

Maturity when described: Hard ripe, Aug. 14, 1990.
Date of first picking: Aug. 10, 1990.
Date of last picking: Aug. 14, 1990.
Size: Uniform, large.
*Average diameter axially.*—2 5/8" [66.7 mm.].
*Average traversely in suture plane.*—2 11/16" [63.3 mm].
Form: Uniform, mostly symmetrical, globose.
*Longitudinal section form.*—Round to slightly oval.
*Transverse section through diameter.*—Round.
Suture: An inconspicuous shallow line extending from the base to the apex, with a slight depression at the apex.
Ventral Surface: Rounded, lipped toward the apex.
Lips: Slightly unequal.
Cavity: Flaring, circular, suture showing on both sides.
*Depth.*—7/16" [11.1 mm.].
*Breadth.*—5/8" [15.9 mm.].
Base: Slightly truncate, with slight stem markings typical.
Apex: Rounded.
Pistil point: Mostly oblique, negligible in length, depressed within the suture.
Stem: Medium.
*Average length.*—3/8 " [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—None observed as of yet.
*Color.*—Deep red [13. deep R] with some very deep red [14. v.deep R] streaking.

Flesh:
*Color.*—Brilliant yellow [83. brill.Y] with some moderate red [15. m.R] streaking most prevalent near the stone and close to the skin surface.
*Amygdalin.*—Scarce.
*Juice.*—Abundant, rich.
*Texture.*—Very firm, very crisp.
*Fibers.*—Abundant, fine.
*Ripens.*—Evenly.
*Flavor.*—Sweet and subacid.
*Aroma.*—Pronounced.
*Eating quality.*—Very good.

STONE

Type: Clingstone.
Form: Oblong.
Base: Slightly oblique.
Apex: Acute.
Sides: Equal.
Surface: Irregularly furrowed toward the apex and pitted toward the base.
Ridges: Jagged toward the base.
Color: Moderate brown [58. m.Br].
Pit wall: ¼" [6.4 mm.] thick.
Tendency to split: None observed.
Kernel:
*Form.*—Oval.
*Taste.*—Sweet.
*Viable.*—Yes.
*Average width.*—½" [12.7 mm.].
*Average length.*—¾" [19.1 mm.].
*Color.*—Light yellow [86. 1.Y] when first cracked.
*Pellicle color.*—Light grayish brown [60. 1.gy.Br].
*Amygdalin.*—Scant.

USE

Market: Fresh and long distance shipping.
Keeping quality: Excellent.
Shipping quality: Excellent
Resistance to insects: No unusual susceptibilities noted.
Resistance to diseases: No Unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to the August Red Nectarine (U.S. Plant Pat. No. 6,363), by producing clingstone nectarines that are very firm in texture and large in size, but is distinguished therefrom and an improvement thereon by producing fruit that is full red in color, ripens 12 days earlier, and is sweeter in flavor.

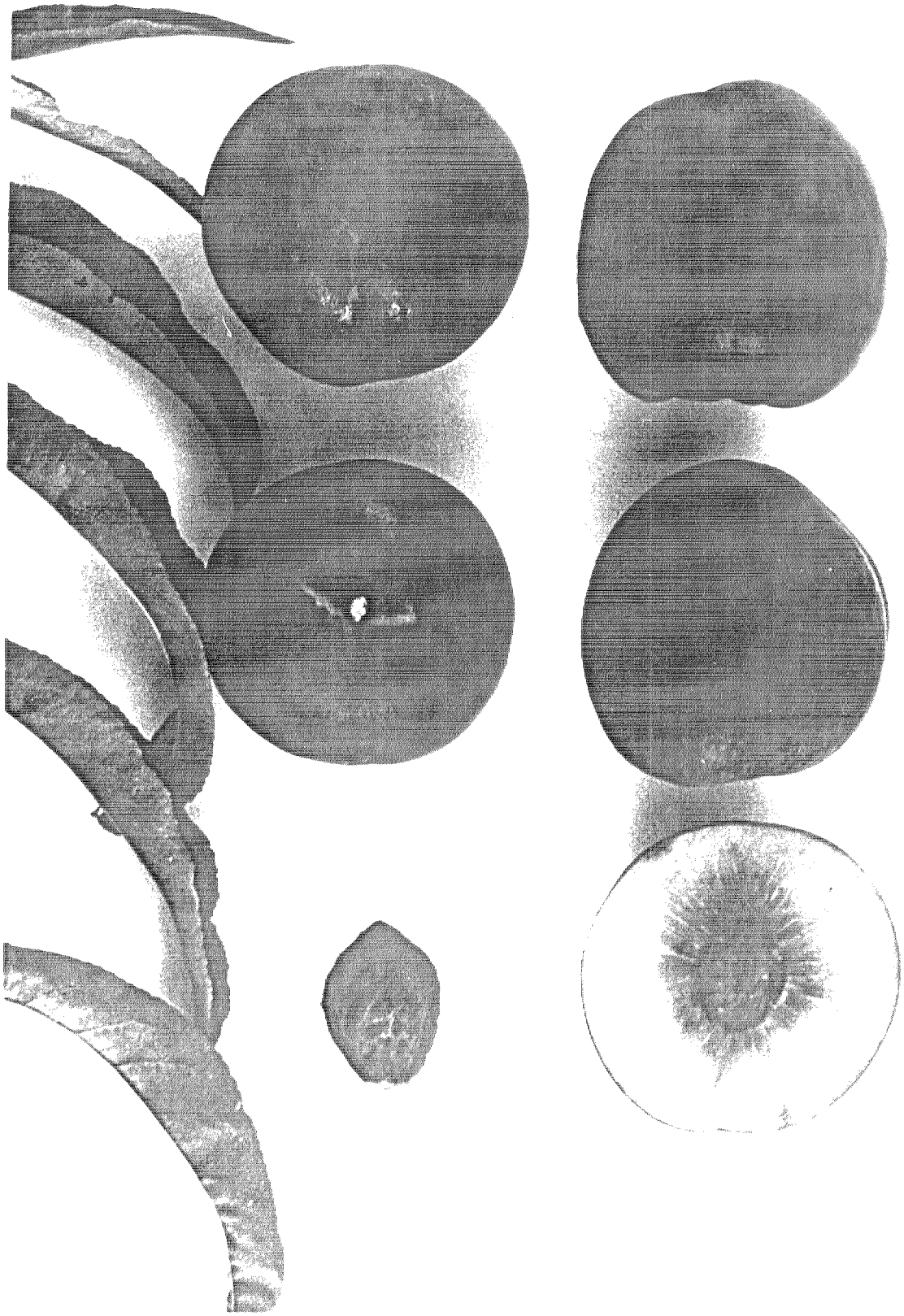

* * * * *